(12) United States Patent
Vincent

(10) Patent No.: US 7,001,362 B2
(45) Date of Patent: Feb. 21, 2006

(54) SYRINGE FOR VISCO-ELASTIC SOLUTIONS

(75) Inventor: Patrice Vincent, Mevoisins (FR)

(73) Assignee: Laboratoire de Contactologie Appliquee-LCA, Chartres (FR)

( * ) Notice: Subject to any disclaimer, the term of this patent is extended or adjusted under 35 U.S.C. 154(b) by 0 days.

(21) Appl. No.: 10/472,804

(22) PCT Filed: Mar. 26, 2002

(86) PCT No.: PCT/FR02/01035

§ 371 (c)(1),
(2), (4) Date: Feb. 10, 2004

(87) PCT Pub. No.: WO02/076534

PCT Pub. Date: Oct. 3, 2002

(65) Prior Publication Data

US 2004/0116871 A1    Jun. 17, 2004

(30) Foreign Application Priority Data

Mar. 7, 2001    (FR) ................... 01 04090

(51) Int. Cl.
*A61M 5/00*    (2006.01)
*A61M 31/00*    (2006.01)

(52) U.S. Cl. .................... 604/191; 604/521

(58) Field of Classification Search ............... 604/191, 604/200, 201, 202, 203, 205, 521, 82, 86–91
See application file for complete search history.

(56) References Cited

U.S. PATENT DOCUMENTS

| | | | | |
|---|---|---|---|---|
| 3,911,916 A | * | 10/1975 | Stevens ........................ | 604/191 |
| 4,067,333 A | * | 1/1978 | Reinhardt et al. ........... | 604/191 |
| 4,188,949 A | * | 2/1980 | Antoshkiw .................... | 604/191 |
| 4,439,184 A | * | 3/1984 | Wheeler ....................... | 604/90 |
| 4,496,344 A | * | 1/1985 | Kamstra ....................... | 604/90 |
| 4,702,737 A | | 10/1987 | Pizzino | |
| 4,715,854 A | * | 12/1987 | Vaillancourt ................ | 604/191 |
| 4,929,230 A | * | 5/1990 | Pfleger ........................ | 604/90 |
| 5,102,388 A | * | 4/1992 | Richmond .................... | 604/88 |
| 5,166,331 A | * | 11/1992 | della Valle et al. ........ | 536/55.1 |
| 5,599,312 A | * | 2/1997 | Higashikawa ............... | 604/191 |
| 5,720,731 A | * | 2/1998 | Aramata et al. ............. | 604/191 |
| 5,788,670 A | * | 8/1998 | Reinhard et al. ............. | 604/89 |
| 5,792,103 A | * | 8/1998 | Schwartz et al. ............. | 604/82 |
| 5,865,799 A | | 2/1999 | Tanaka et al. | |
| 2002/0035351 A1 | | 3/2002 | Lodice | |
| 2004/0116871 A1 | * | 6/2004 | Vincent ....................... | 604/191 |

FOREIGN PATENT DOCUMENTS

| | | |
|---|---|---|
| EP | 0 695 555 | 2/1996 |
| EP | 0 974 320 | 1/2000 |
| WO | WO 02 11793 | 2/2002 |

OTHER PUBLICATIONS

International Preliminary Examination Report, dated Jun. 30, 2003.

* cited by examiner

*Primary Examiner*—Sharon Kennedy
(74) *Attorney, Agent, or Firm*—Holland & Hart

(57) ABSTRACT

A device for dispensing viscoelastic solutions, said device consisting of a syringe (1) which contains at least two viscoelastic solutions (V1, V2) having different properties, said solutions (V1, V2) being dispensed in succession, in a predetermined order, said device being characterized in that said syringe (1) includes at least one moving diaphragm (10) that separates said at least two viscoelastic solutions (V1, V2).

20 Claims, 1 Drawing Sheet

SYRINGE FOR VISCO-ELASTIC SOLUTIONS

Figure 1:
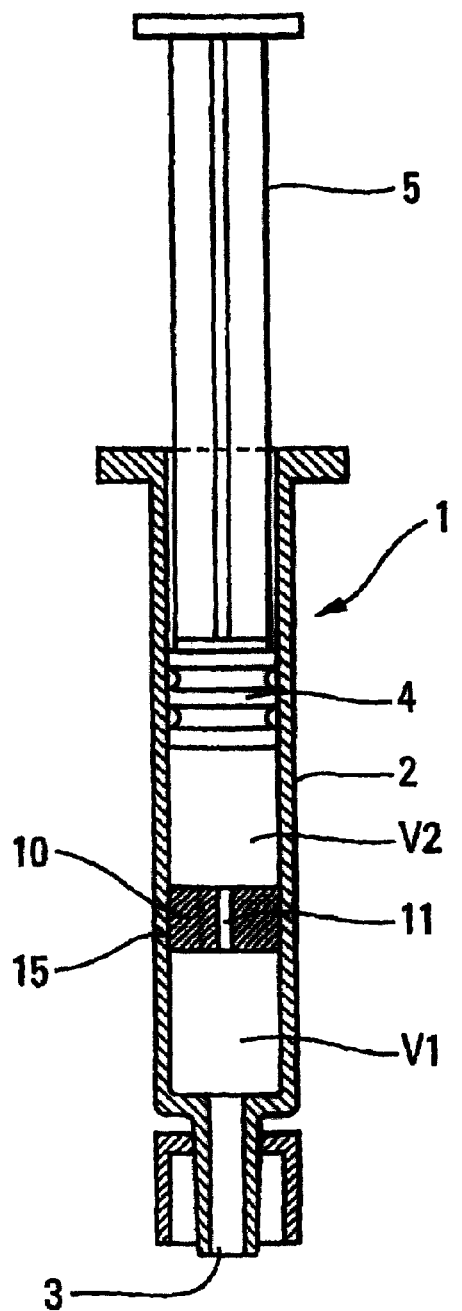

The present invention relates to a syringe for injecting viscoelastic solutions used in medical and surgical fields. Such solutions are currently used in rheumatology in the form of intra-articular injections, in dermatology for filling in wrinkles, in plastic surgery, in abdominal surgery, and in ophthalmological surgery, with it being possible for other uses to emerge in the future.

More particularly, the present invention is applicable during cataract surgery, when an intraocular lens is implanted. In which case, viscoelastic solutions serve to create the spaces necessary for the surgery, and to protect the tissues of the eye, in particular the corneal endothelium. An important condition is that this type of solution must be removed by suction at the end of the operation, failing which it might cause a harmful increase in the intraocular pressure.

In cataract surgery, a substance having dynamic viscosity that is higher at high shear rates is generally used first. This normally applies during the surgical steps known as "capsulorhexis" and "phacoemulsification", which are surgical techniques that are well known to the person skilled in the art. A substance having dynamic viscosity that is lower under similar shear conditions is preferably used second, while the intraocular lens is being implanted.

Currently, it is necessary for the surgeon to manipulate two syringes, each of which contains a distinct viscoelastic solution. The other possibility is to use a single viscoelastic solution. In the former case, the operation is made more complicated by the use of more than one syringe, and in the latter case, the solution used constitutes a poor compromise, and therefore suffers from at least one drawback, namely either it does not stay properly in place during phacoemulsification, or else it is difficult to extract at the end of the operation, after the intraocular lens has been implanted.

An object of the present invention is to provide a syringe for injecting viscoelastic solutions in the medical field that does not suffer from the above-mentioned drawbacks.

In particular, an object of the present invention is to provide a syringe for injecting viscoelastic solutions that simplifies the task of the surgeon, and that makes it possible to use substances having good characteristics at each stage of the operation.

A further object of the present invention is to provide such a syringe for injecting viscoelastic solutions that is simple and inexpensive to manufacture and to assemble.

The present invention thus provides a device for dispensing viscoelastic solutions, said device consisting of a syringe which contains at least two viscoelastic solutions having different properties, said solutions being dispensed in succession, in a predetermined order, said device being characterized in that said syringe includes at least one moving diaphragm that separates said at least two viscoelastic solutions.

Advantageously, said diaphragm includes sealing gaskets.

Advantageously, said moving diaphragm incorporates a preferably small opening enabling the viscoelastic solution disposed upstream from the diaphragm to be discharged after the viscoelastic solution disposed downstream from the diaphragm has been dispensed in full.

In a variant embodiment, said opening is closed off by a membrane, said syringe being provided with opening means, such as a piercing spike, suitable for opening said membrane once the viscoelastic solution disposed downstream from the diaphragm has been dispensed in full.

Advantageously, a small air bubble is disposed in said opening in the diaphragm so as to prevent any contact between the viscoelastic solutions.

Advantageously, said diaphragm is connected via a temporary mechanical coupling to the plunger of the syringe during dispensing of the viscoelastic solution disposed downstream from the diaphragm, said temporary mechanical coupling being eliminated once said viscoelastic solution has been dispensed in full, so as to enable the viscoelastic solution disposed upstream from the diaphragm to be dispensed.

Advantageously, said at least two viscoelastic solutions have different rheological properties.

Advantageously, said at least two viscoelastic solutions have different chemical compositions and/or different molecular weights of their active principles and/or different concentrations of their active principles.

Advantageously, said at least two viscoelastic solutions have dynamic viscosities that are different at high shear rates.

The present invention also provides the use of the syringe as defined above in cataract surgery.

Figure 2:
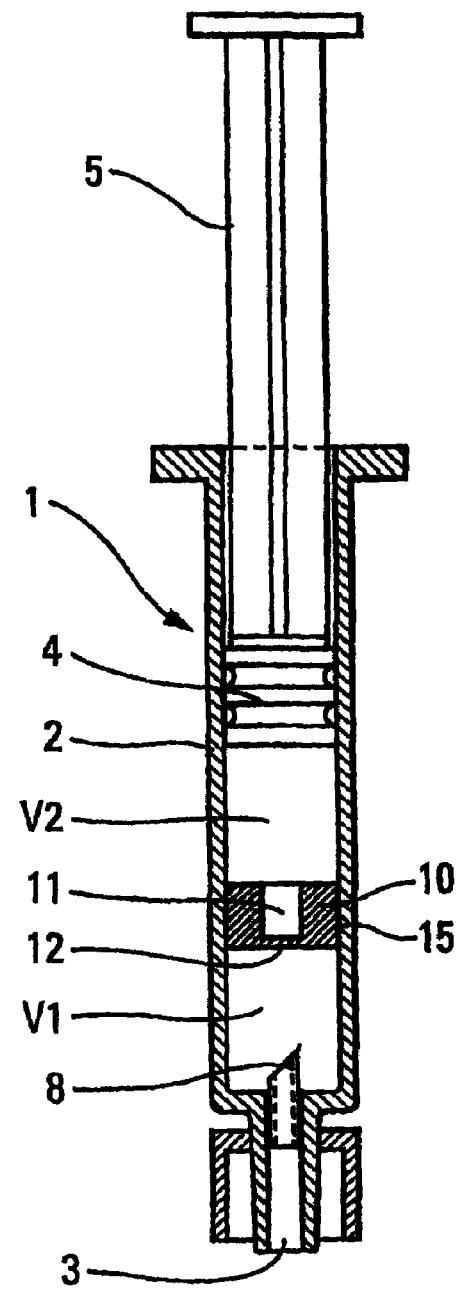

Other characteristics and advantages of the present invention will appear more clearly on reading the following detailed description of two advantageous embodiments thereof, given with reference to the accompanying drawing which is given by way of non-limiting example, and in which:

FIG. 1 is a diagrammatic view in section of a first embodiment of a syringe of the present invention; and FIG. 2 is a diagrammatic view in section of a second embodiment of a syringe of the present invention.

In general, a syringe 1 comprises a generally cylindrical syringe body 2 provided firstly with a dispensing orifice 3 and secondly with a plunger 4 actuated by an actuating rod 5. The user presses on the actuating rod 5 to move the plunger 4 inside the body 2 for the purpose of dispensing the substance contained in the syringe through the dispensing orifice 3.

In the invention, the syringe 1 contains at least two viscoelastic solutions V1, V2 which have different properties, said solutions V1, V2 being dispensed in succession in a predetermined order.

More particularly, the at least two viscoelastic solutions V1, V2 differ in their chemistry and/or in the molecular weights of their active principles and/or in the concentrations of said active principles. More generally, the viscoelastic solutions of the present invention have different rheological properties, and advantageously they have different dynamic viscosities, at high shear rates.

In the invention, provision is made to interpose a moving diaphragm 10 between the solutions V1, V2. The diaphragm 10 is preferably provided with sealing gaskets 15 on its outside periphery, which gaskets co-operate with the body 2 of the syringe 1. Thus, the diaphragm 10 can slide against the inside wall of the syringe body in leaktight manner, while being guided like the plunger in the syringe. As the first viscoelastic solution V1 is dispensed, the diaphragm 10 moves at the same time as the plunger 4 under the effect of the thrust that is transmitted by the second viscoelastic solution V2. In a variant, it is possible to imagine a temporary mechanical coupling that connects the diaphragm 10 to the plunger 4 for the purpose of displacing these two elements simultaneously while the first viscoelastic solution VI is being discharged, said mechanical coupling being eliminated when the second viscoelastic solution V2 is dispensed.

In order to enable the second viscoelastic solution V2 to be dispensed, the diaphragm 10 is provided with an opening 11 that is preferably disposed centrally and that is preferably small in size. This is generally sufficient to prevent the solutions V1 and V2 from mixing before the solution V1 is dispensed in full, as shown in the example in FIG. 1, even if said opening 11 is not closed off.

Thus, when the user presses on the actuating rod 5, firstly the first solution V1 is discharged through the dispensing orifice 3, then the diaphragm comes into abutment against the end wall of the body 2 of the syringe, and the second viscoelastic solution V2 is then discharged through the opening 11 in the diaphragm. In order for the syringe to operate properly, the force to be exerted to cause the second viscoelastic solution V2 to pass through the small opening 11 must generally be greater than the friction between the diaphragm 10 and the wall of the syringe, with the presence of the mechanical coupling being taken into account when applicable. The presence of a small interface of air inside the opening 11, e.g. a captive small air bubble, advantageously makes it possible to prevent any contact between the two solutions until they are used.

In the embodiment shown in FIG. 2, the diaphragm 10 is shown to be fully leaktight, with a membrane 12 that closes off the opening 11 which can then be larger than in the embodiment shown in FIG. 1. This implementation may be considered when the solutions V1 and V2 tend to mix, e.g. merely by returning to osmotic equilibrium or while the first solution V1 is being dispensed. The syringe 1 is then provided with opening means such as piercing spike 8 adapted to opening said membrane 12 when the diaphragm 10 comes into contact with the end-wall of the syringe, i.e. once the first viscoelastic solution V1 which is disposed downstream from the diaphragm has been dispensed in full.

In this way, contact is totally prevented between the two solutions V1 and V2 prior to and during actuation of the device.

As shown diagrammatically in the drawing, at its dispensing opening 3, the syringe may be provided with a Luer Lock secure connection system that makes it possible to lock an injection needle or cannula to the end-piece of the syringe.

As mentioned above, a particularly advantageous use of the present invention relates to cataract surgery, but the present invention is not limited to such a use.

Although the present invention is described with reference to two advantageous embodiments thereof, it is not limited by the examples shown, and the person skilled in the art may make any modifications to it without going beyond the ambit of the present invention, as defined by the accompanying claims.

What is claimed is:

1. A device for dispensing viscoelastic solutions, said device consisting of a syringe (1) formed with a single body which contains at least two viscoelastic solutions (V1, V2) having different properties, said solutions (V1, V2) being dispensed in succession, in a predetermined order, said viscoelastic solutions being separated by a single moving diaphragm only incorporating a small opening (11) enabling the viscoelastic solution (V2) disposed upstream from the diaphragm (10) to be discharged after the viscoelastic solution (V1) disposed downstream from the diaphragm (10) has been dispensed in full.

2. A device according to claim 1, in which said diaphragm (10 includes sealing gaskets (15).

3. A device according to claim 1, in which a small air bubble is disposed in said opening (11) in the diaphragm (10) so as to prevent any contact between the viscoelastic solutions (V1, V2).

4. A device according to claim 1, in which said at least two viscoelastic solutions (V1, V2) have different reheological properties.

5. A device according to claim 1, in which said at least two viscoelastic solutions (V1, V2) have different chemical compositions and/or different molecular weights of their active principles and/or different concentrations of their active principles.

6. A device according to claim 1, in which said at least two viscoelastic solutions have dynamic viscosities that are different at high shear rates.

7. A method of dispensing viscoelastic solutions into an eye, the method comprising the steps of:
   selecting the device of claim 1; establishing fluid communication between an eye and the device; and
   sequentially dispensing the viscoelastic solutions into the eye.

8. A device according to claim 2, in which a small air bubble is disposed in said opening (11) in the diaphragm (10) so as to prevent any contact between the viscoelastic solutions (V1, V2).

9. A device according to claim 2, in which said at least two viscoelastic solutions (V1, V2) have different rheological properties.

10. A device according to claim 3, in which said at least two viscoelastic solutions (V1, V2) have different rheological properties.

11. A device according to claim 1, in which said at least two viscoelastic solutions (V1, V2) have different rheological properties.

12. A device according to claim 2, in which said at least two viscoelasatic solutions (V1, V2) have different chemical compositions and/or different molecular weights of their active principles and/or different concentrations of the active principles.

13. A device according to claim 3, in which said at least two viscoelastic solutions (V1, V2) have different chemical compositions and/or different molecular weights of their active principles and/or different concentrations of their active principles.

14. A device according to claim 1, in which said at least two viscoelastic solutions (V1, V2) have different chemical compositions and/or different molecular weights of their active principles and/or different concentrations of their active principles.

15. A device according to claim 4, in which said at least two viscoelastic solutions (V1, V2) have different chemical compositions and/or different molecular weights of their active principles and/or different concentrations of their active principles.

16. A device according to claim 2, in which said at least two viscoelastic solutions have dynamic viscosities that are different at high shear rates.

17. A device according to claim 3, in which said at least two viscoelastic solutions have dynamic viscosities that are different at high shear rates.

18. A device according to claim 1, in which said at least two viscoelastic solutions have dynamic viscosities that are different at high shear rates.

19. A device according to claim 4, in which said at least two viscoelastic solutions have dynamic viscosities that are different at high shear rates.

20. A device according to claim 5, in which said at least two viscoelastic solutions have dynamic viscosities that are different at high shear rates.

* * * * *